United States Patent
Zhao et al.

(12)

(10) Patent No.: US 6,747,145 B2
(45) Date of Patent: Jun. 8, 2004

(54) PHOTOCHROMIC BIS-NAPHTHOPYRAN COMPOUNDS AND METHODS FOR THEIR MANUFACTURE

(75) Inventors: Weili Zhao, Zurich (CH); Erick M. Carreira, Zumikon (CH)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 206 days.

(21) Appl. No.: 09/945,897

(22) Filed: Sep. 4, 2001

(65) Prior Publication Data

US 2003/0078441 A1 Apr. 24, 2003

(51) Int. Cl.$^7$ ............................................. C07D 417/14
(52) U.S. Cl. ........................ 544/61; 544/150; 546/209; 546/280.4; 546/282.7; 548/527; 549/13; 549/389; 365/119
(58) Field of Search ................... 544/61, 150; 546/209, 546/280.4, 282.7; 548/527; 549/13, 389

(56) References Cited

U.S. PATENT DOCUMENTS

| | | |
|---|---|---|
| 3,567,605 A | 3/1971 | Becker |
| 5,066,818 A | 11/1991 | Gemert et al. |
| 5,451,814 A | 9/1995 | Yoshimizu |
| 5,645,767 A | 7/1997 | Gemert |
| 5,952,515 A | 9/1999 | Melzig et al. |
| 6,281,366 B1 | 8/2001 | Frigoli et al. |

FOREIGN PATENT DOCUMENTS

WO    WO 96/01884 A    1/1996

OTHER PUBLICATIONS

Yassar et al., Synthetic Metals, vol. 124, No. 1(2001), pp. 23–27, published Apr. 2001.*
PCT International Search Report, dated Nov. 27, 2002, for PCT Int'l. Appln. No. PCT/US02/25669.
Moustrou, Corrine et al., "Synthesis of Thiophane–Substituted 3H–Naphtho[2,1–b]pyrans, Precursors of Photomodulated Materials", *Helvetica Chimica Acta*, Verleg Helvetica Chimica Acta Basel, CH, vol. 81, No. 7, pp. 1293–1302 (1998).
Samat, Andre et al., "Synthesis and Unexpected Photochemical Behaviour of Biphotochromic Systems Involving Spirooxazines and Naphthopyrans Linked by an Ethylenic Bridge", Tetrahedron, Elsevier Science Publishers, Amsterdam, NL, vol. 57, No. 34, pp. 7349–7359 (2001).
Yassar, A. et al., "Molecular Switch Devices Realised By Photochromic Oligothiophenes", Synthetic Metals, vol. 124, No. 1, pp. 23–27 (2001).
Zhao, Weili et al., "A Smart Photochromophore Through Synergistic Coupling fo Photochromic Subunits", Journal of the American Chemical Society, vol. 124, No. 8, pp. 1582–1582 (2002).

* cited by examiner

*Primary Examiner*—Joseph K. McKane
*Assistant Examiner*—Kamal Saeed

(57) ABSTRACT

The invention provides photochromic bis-naphthopyran compounds as well as methods for their manufacture and their use. The bis-naphthopyran compounds of the invention exhibit a wide range of color, i.e., from pink to purple to blue gray, upon activation by a source of UV light. Additionally, the bis-naphthopyran compounds of the present invention exhibit broad coloration ability, fast response as to both color change on activation and return to original color, and good fatigue-resistance.

4 Claims, No Drawings

PHOTOCHROMIC BIS-NAPHTHOPYRAN COMPOUNDS AND METHODS FOR THEIR MANUFACTURE

FIELD OF THE INVENTION

The present invention relates to photochromic naphthopyran compounds. More particularly, this invention provides photochromic bis-naphthopyran compounds as well as methods for their manufacture and their use.

BACKGROUND OF THE INVENTION

Several types of photochromic compounds are known for use in applications in which reversible color change, or darkening, induced by sunlight is desirable. These applications include for example, ophthalmic lenses, solar protection lenses, filters, camera optical systems, decorative objects, windows and the like.

However, the known compounds are disadvantageous in that they do not exhibit both high optical density and the ability to return to their original color quickly once the activating light source is removed. Thus, there is a need for new compounds with fast response to ultraviolet ("UV") irradiation, high colorability and long lifetime.

DETAILED DESCRIPTION OF THE INVENTION AND PREFERRED EMBODIMENTS

The present invention provides bis-naphthopyran compounds that exhibit a wide range of color, i.e., from pink to purple to blue gray, upon activation by a source of UV light and that, when the irradiation is discontinued, the original color is recovered. The bis-naphthopyran compounds of the present invention exhibit broad coloration ability, fast coloration response, and good fatigue-resistance.

In one embodiment, the present invention provides a compound comprising:

Formula (I)

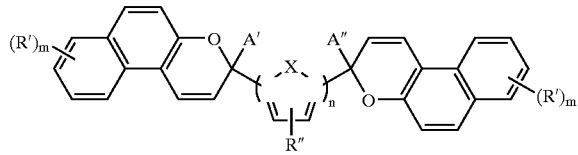

wherein X is sulfur or oxygen;

R', R" may be the same or different and are each independently hydrogen, hydroxy, halogen, nitro, cyano, allyl, linear or branched $(C_1-C_{20})$alkyl, $(C_3-C_{20})$ cycloalkyl, $(C_1-C_{20})$alkoxy, $(C_1-C_{20})$alkylacetylenyl, phenylacetylenyl, $(C_1-C_{20})$alkenyl, phenylvinyl, halo $(C_1-C_{20})$alkyl, halo$(C_3-C_{20})$cycloalkyl, halo$(C_1-C_{20})$ alkoxy, aryl, aryloxy or heteroaryl optionally substituted with $(C_1-C_6)$alkyl or $(C_1-C_6)$alkoxy; arylalkyl or heteroarylalkyl; nitrogen-containing heterocyclic ring having 5 or 6 atoms optionally substituted with $(C_1-C_6)$ alkyl or $(C_1-C_6)$alkoxy, —$N(R_1)R_2$, $CON(R_1)R_2$, wherein $R_1$ and $R_2$ may be the same or different and are each independently hydrogen, $(C_1-C_{20})$alkyl, $(C_3-C_{20})$ cycloalkyl, and optionally substituted phenyl; —OCOR, —COOR or —COR, wherein R represents hydrogen, $(C_1-C_{20})$alkyl, $(C_3-C_{20})$cycloalkyl, or aryl or heteroaryl optionally substituted with $(C_1-C_6)$alkyl or $(C_1-C_6)$alkoxy;

A', A" may be same or different and are each independently:
(a) linear or branched $(C_1-C_{12})$alkyl, $(C_3-C_{12})$ cycloalkyl, aryl$(C_1-C_6)$alkyl or heteroaryl$(C_1-C_6)$ alkyl, $(C_1-C_6)$alkoxy$(C_1-C_6)$alkyl, $(C_1-C_{12})$alkoxy, halo$(C_1-C_{12})$alkyl, $(C_1-C_{12})$haloalkoxy, $(C_1-C_{12})$ alkylthio;
(b) substituted or unsubstituted aryl groups;
(c) substituted or unsubstituted heteroaryl groups;
(d) a group of the following formulae:

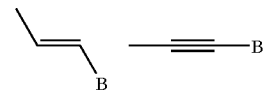

wherein B is hydrogen, $(C_1-C_{12})$alkyl or substituted or unsubstituted aryl;
(e) unsubstituted or mono-substituted pyrazolyl, pyridyl, imidazolyl, pyrazolinyl, imidazolinyl, or acridinyl, each of the said substituents being $(C_1-C_6)$ alkyl, $(C_1-C_6)$alkoxy, fluoro, chloro, or phenyl.
(f) a group of the following formulae:

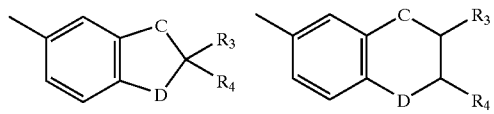

wherein C and D may be the same or different and are each independently carbon, oxygen, $(C_1-C_{12})$ alkyl nitrogen, or $(C_1-C_{12})$acyl nitrogen;
$R_3$ and $R_4$ are each hydrogen or $(C_1-C_{12})$alkyl; and wherein the phenyl moiety is optionally substituted with $(C_1-C_{12})$alkyl, $(C_1-C_{12})$alkoxy, $(C_2-C_{12})$acyl, fluoro, or chloro;
n is an integer from 1 to 8; and
m is an integer from 0 to 3.

"Nitrogen-containing heterocyclic ring having 5 or 6 atoms" includes, without limitation, pyrrolidino, piperidino, morpholino, and the like. "Halogen" or "halo" means fluoro, chloro, bromo, or iodo. Preferably fluoro, chloro, or bromo is used. "Aryl" includes, without limitation, phenyl or naphthyl. "Heteroaryl" includes, without limitation, furyl, thienyl, pyrryl, indolyl, benzofuryl, benzothienyl, pyridyl, dibenzofuryl, dibenzothienyl, and carbazolyl.

"Substituted aryl or heteroaryl groups" includes, without limitation aryl or heteroaryl groups that are mono-, di-, or tri-substituted by a substituent that is: halogen nitro, amino, cyano, hydroxy, epoxy, vinyl, allyl, hydroxyethoxy, methoxyethoxy, hydroxyethoxyethoxy, methoxyethoxyethoxy; $(C_1-C_{12})$alkyl, $(C_1-C_{12})$alkoxy, $(C_1-C_{12})$alkylaryl, aryl, aryloxy, aryl$(C_1-C_{12})$alkyl, aryl$(C_1-C_{12})$alkoxy, $(C_1-C_{12})$alkoxyaryl, halo$(C_1-C_{12})$alkyl, haloaryl, cyclo $(C_3-C_{12})$alkyl, cyclo$(C_1-C_{12})$alkoxy, aryloxyaryl, aryloxy $(C_1-C_{12})$alkyl, aryloxy$(C_1-C_{12})$alkoxy, acryloxy, methacryloxy; a heterocyclic nitrogen-containing substituent, such as N-$(C_1-C_{12})$alkylpiperazino, N-aryl-piperizino, aziridino, indolino, pyrrolidino, pyrrolino, piperidino, $(C_1-C_4)$ alkylpiperidino, di$(C_1-C_4)$alkylpiperidino, 4-piperidinopiperidino, morpholino, 2,6-di$(C_1-C_4)$ alkylmorpholino, thiomorpholino, thioazolidino, tetrahydroquinolino, pyrryl; —$N(R_1)R_2$, $CON(R_1)R_2$, wherein $R_1$ and $R_2$ are the same or different and are independently hydrogen, $(C_1-C_{12})$alkyl, $(C_3-C_{12})$ cycloalkyl, phenyl, mono- or di-substituted phenyl; or —COR, —OCOR or —COOR, wherein R is hydrogen, $(C_1-C_{12})$alkyl, $(C_3-C_{12})$cycloalkyl, halo$(C_1-C_6)$alkyl, unsubstituted, mono- or di-substituted phenyl, unsubstituted, mono- or di-substituted naphthyl, unsubstituted, mono- or di- substituted furyl, or thienyl, and combination thereof.

In a preferred embodiment, the present invention provides a compound of Formula I wherein:

X is sulfur or oxygen;

R', R" are the same or different and are each independently hydrogen, nitro, cyano, allyl, fluoro, chloro, bromo, trifluoromethyl, trichloromethyl, pyrrolidino, piperidino, morpholino, phenyl, benzyl; linear or branched $(C_1-C_6)$alkyl, $(C_1-C_6)$alkoxy, or —OCOR or —COOR wherein R is hydrogen, $(C_1-C_6)$alkyl, $(C_3-C_6)$cycloalkyl;

A', A" are the same or different and are each independently:
(a) linear or branched $(C_1-C_6)$alkyl, $(C_3-C_6)$cycloalkyl, aryl$(C_1-C_4)$alkyl or heteroaryl$(C_1-C_4)$alkyl, $(C_1-C_6)$alkoxy$(C_1-C_6)$alkyl;
(b) unsubstituted, mono-, di-substituted aryl selected from phenyl or naphthyl, preferably substituted in the meta position, the para position, or both;
(c) unsubstituted or mono-substituted heteroaryl groups that are furyl, thienyl, pyrryl, indolyl, benzofuryl, benzothienyl, pyridyl, dibenzofuryl, dibenzothienyl, or carbazolyl the substituents being nitro, amino, cyano, hydroxy, epoxy, hydroxyethoxy, methoxyethoxy, hydroxyethoxyethoxy, methoxyethoxyethoxy, fluoro, chloro, bromo, iodo, vinyl, allyl, trifluoromethyl, phenyl, $(C_1-C_6)$alkyl, $(C_1-C_6)$alkoxy, cyclo$(C_3-C_6)$alkyl, cyclo$(C_1-C_6)$alkoxy, $(C_1-C_6)$)alkylamino, di$(C_1-C_6)$alkylamino, diarylamino, phenylacetylenyl, or phenylvinyl;
a heterocyclic nitrogen-containing substituent, such as N$(C_1-C_6)$alkylpiperazino, N-aryl-piperizino, aziridino, indolino, pyrrolidino, pyrrolino, piperidino, $(C_1-C_4)$alkylpiperidino, di$(C_1-C_4)$alkylpiperidino, 4-piperidinopiperidino, morpholino, 2,6-di$(C_1-C_4)$alkylmorpholino, thiomorpholino, thioazolidino, tetrahydroquinolino, or pyrryl;
N$(R_1)R_2$, CON$(R_1)R_2$, wherein $R_1$ and $R_2$ are the same or different and are each independently hydrogen, $(C_1-C_6)$alkyl, $(C_3-C_6)$cycloalkyl, phenyl or —COR, —OCOR or —COOR wherein R is hydrogen, $(C_1-C_6)$alkyl, $(C_3-C_6)$cycloalkyl, or phenyl;

n is an integer from 1 to 6; and m is an integer from 0 to 2.

In a still more preferred embodiment, the invention provides a compound of Formula I wherein:

X is sulfur;

R', R" are the same or different and are each independently hydrogen, nitro, cyano, fluoro, chloro, bromo, pyrrolidino, piperidino, morpholino, phenyl, benzyl, $(C_1-C_4)$alkyl, or $(C_1-C_4)$alkoxy;

A', A" are the same or different and are each independently:
a linear or branched $(C_1-C_4)$alkyl, $(C_3-C_6)$cycloalkyl;
unsubstituted, mono-, or di-substituted phenyl, preferably substituted in the meta position, para position or both with the substituents being one or more of nitro, amino, acyl, cyano, methoxy, ethoxy, methoxyethoxy, fluoro, chloro, vinyl, allyl, methoxycarbonyl, ethoxycarbonyl, $(C_1-C_4)$alkyl, di$(C_1-C_4)$alkylamino, piperazino, piperidino, arylperidino, morpholino, pyrrolidino, aziridino, acryloxy, methacryloxy, phenylacetylenyl, phenylvinyl;
unsubstituted, mono-substituted heteroaromatic groups, such as furyl, thienyl, pyrryl, substituted with a substituent that is $(C_1-C_4)$alkyl or phenyl;

n is an integer from 1 to 4, and m is, independently, integer from 0 to 2.

In a yet more preferred embodiment, the compound of the invention is:

5,5'-Bis[3-(p-methoxyphenyl)-[3H]-naphtho[2,1-b]pyran-3-yl]-2,2'-bithiophene;

5,5'-Bis[3-(p-methylphenyl)-[3H]-naphtho[2,1-b]pyran-3-yl]-2,2'-bithiophene;

5,5'-Bis[3-(p-fluorophenyl)-[3H]-naphtho[2,1-b]pyran-3-yl]-2,2'-bithiophene;

5,5'-Bis[3-(o-fluorophenyl)-[3H]-naphtho[2,1-b]pyran-3-yl]-2,2'-bithiophene;

5,5'''-Bis[3-(p-methoxyphenyl)-[3H]-naphtho[2,1-b]pyran-3-yl]-[2,2',5',2'',5'',2'''[-quaterthiophene;

5,5'''-Bis[3-(naphthalene-2-yl)-[3H]-naphtho[2,1-b]pyran-3-yl]-[2,2',5',2'',5'',2'''[-quaterthiophene; or 5,5'''-Bis[3-(o-fluorophenyl)-[3H]-naphtho[2,1-b]pyran-3-yl]-[2,2',5',2'',5'',2'''[-quaterthiophene.

The compounds of Formula I may be prepared by the process illustrated in Reactions A through D below or, alternatively, in a process illustrated in Reaction E. In Reaction A, the corresponding aromatic ketone is formed from an acid chloride and the reaction may be the following Friedel-Crafts reaction:

Reaction A:

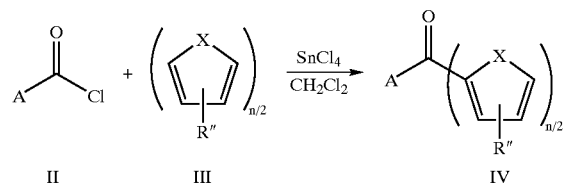

The acid chloride represented by Formula II and heterocyclic compound represented by Formula III are dissolved in dichloromethane and reacted in the presence of a Lewis acid, such as stannous chloride, to form the corresponding substituted aromatic ketone represented by Formula IV. The substituents A, R", X and n are the same as defined hereinabove. The Friedel-Crafts reaction, and the conditions for carrying it out, are described in Olah, George A., 3 *"Friedel-Crafts and Related Reactions,"* Interscience Publishers (1964).

In Reaction B, the heteroaromatic ketone of Formula IV is reacted with sodium acetylide in a suitable solvent, such as anhydrous tetrahydrofuran ("THF"), dimethylsulfoxide ("DMSO") or the like, to form the corresponding propargyl alcohol represented by graphic formulae V.

Reaction B:

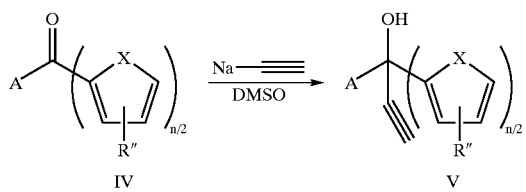

The reaction may be conducted at room temperature in a 1 to 100 mmol scale.

In Reaction C, the propargyl alcohol of Formula V may be coupled with a naphthol represented by Formula VI in the presence of a catalytic amount of acid, such as pyridinium p-toluenesulfonate ("PPTS"), to generate naphthopyran represented by graphic formulae VII. This reaction and the conditions for carrying it out are described in *Helv Chim. Acta*, 81 (7), 1293 (1998).

Reaction C:

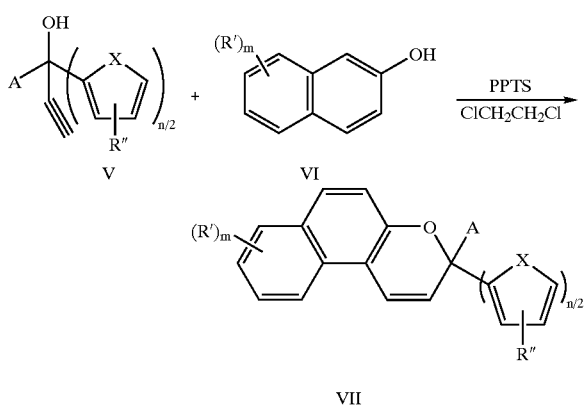

Alternatively and preferably, Reaction C may be carried out using 3 Å molecular sieves. This reaction may be performed in the presence of a non-polar solvent, preferably benzene, toluene, xylene, chloroform, 1,1-dichlorethane, 1,2-dichloroethane, carbon tetrachloride, or a combination thereof. More preferably, the reaction is performed in toluene or 1,2-dichloroethane. The reaction temperatures may be from about 50 to about 160° C., preferably about 80 to about 140° C., more preferably about 90 to 120° C. Reaction time may be about 1 hour to about 3 days, preferably about 2 hours to about 2 days, and more preferably about 2 hours to about 24 hours. The preferred ratio of reactants is 1.1:1:0.5 to about 1:1.1:0.05 (V:VI:PPTS).

In Reaction D, the naphthopyran of Formula VII is treated with butyl lithium and then cupric chloride in a suitable solvent, such as anhydrous THF, and generate the homo-coupled product represented by Formula I.

Reaction D:

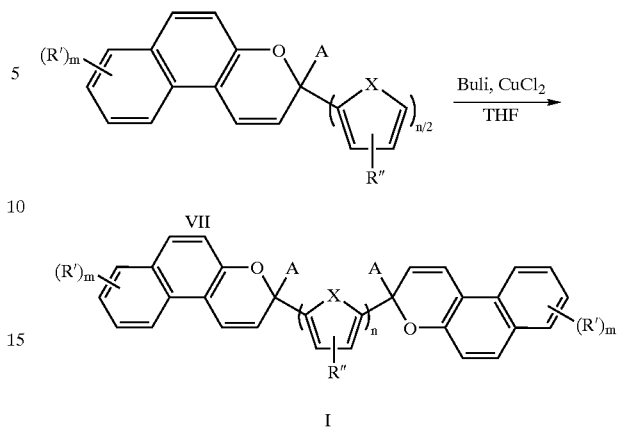

The reaction may be carried out at between about −78° C. and ambient temperatures for about 5 to about 48 hours. The reactants preferably are used in a ratio of about 1:1.1:1.1 to about 1:1.5:2 (VII:BuLi:CuCl$_2$).

Alternatively, the bis-naphthopyran compound of the invention may be prepared in as shown in Reaction E. In Reaction E, a bis-heteroaromatic ketone of Formula IX may be generated by Friedel-Crafts reaction of a heterocyclic compound of Formula III. Upon treatment with sodium acetylide, the desired bis-propargyl alcohol of Formulae IV may be generated. Coupling of the bis-propargyl alcohol of Formula X with naphthol of Formulae VI in the presence of a catalytic amount of an acid such as pyridinium p-toluenesulfonate ("PPTS"), generates the desired bis-naphthopyran compound.

Reaction E:

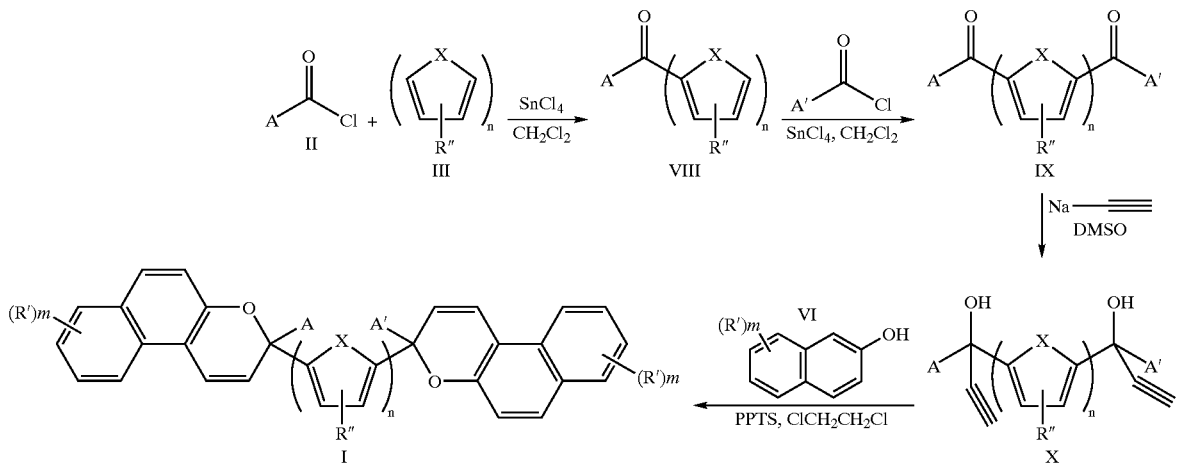

The bisnaphthopyran compounds of the invention may be used alone or as a mixture with other compounds of Formula I. Additionally, the compounds of the invention mat be used in a mixture with other types of known photochromic compounds including, without limitation, naphthopyran, spirooxazine, mixtures with one or more nonphotochromic dyes, or combinations thereof. In addition one or more stabilizers, such as an antioxidant, one or more UV absorbent such as 2-hydroxyphenylbenzotriazoles or 2-hydrpxyphenyltriazones, one or more anti radical agents such as 5-ethoxybenzoimidazole, or combinations thereof maybe added to these mixtures to improve photochromic properties.

One particular advantage of the compounds of the present invention is that the absorption spectra of the colored form of the activated bisnaphthopyran compounds of Formula I typically exhibit higher optical densities or absorbances, and longer lifetime, than the corresponding photochromic naphthopyrans of Formula VII. In solution, the compounds of the invention are pale pink or yellow. When activated by a source of UV radiation, such as solar radiation or light from a mercury or xenon lamp, solutions of the bis-naphthopyran compounds of the invention rapidly develop an intense coloration, depending on the structure of compound, ranging from pink to purple to blue gray. The response of bis-naphthopyran of Formula I to UV irradiation is much faster than that of naphthopyran represented by graphic formulae VII shown in Reaction C.

A wide variety of fading ranging from 3 seconds to 300 seconds depending on the structure of bis-naphthopyran compounds is also provided. When the fade is slow, or longer than 100 seconds, the bis-naphthopyran compounds of Formula I exhibit high colorability due to the fully opening of the two photochromic functionalities in the bis-naphthopyran. To obtain a slow fading compound, a fluoro substituent is placed in the ortho position of the 3-phenyl group. Slow fading is desirable for certain uses including, without limitation, windows.

When the fade is fast, or less than 60 seconds, the bis-naphthopyran compound of the invention provide higher optical density and longer life-time than the corresponding photochromic naphthopyrans represented by Formulae VII. Fast fading is obtained without substitution at the ortho position and, optionally, by placing a substituent at the para postion of the 3-phenyl group. Suitable substituents include, without limitation, fluoro, methoxy, methyl, ethyl, phenyl, piperidino, or morpholino. Fast fading is useful in a wide variety of setting including, without limitation, in spectacle lenses.

The bis-naphthopyran compounds of the invention alone, mixtures thereof, or mixtures of these with other types of known photochromic compounds may be introduced into a composition that can be applied to or introduced into a host material. The compositions may include inks or coating compositions. The photochromic bis-naphthopyran compounds may be present in an organic solvent or an organic polymer host.

If a solvent is used, the solvent may be any solvent capable of dissolving the photochromic substances. Suitable solvents include, without limitation, benzene, toluene, methyl ethylketone, acetone, ethanol, methanol, propanol, isopropanol, tetrahydrofuran, dioxane, ethyl acetate, ethylene glycol, xylene, cylcohexane, N-methyl pyrrolidinone, and the like, and mixtures thereof. When dissolved in chloroform, the compounds of the invention have a much larger molar extinction coefficient ($\epsilon$) and, thus, can block more UV radiation, than the corresponding naphthopyran precursor represented by Formula VII.

The host materials used with the compounds of the invention may be any materials for which exhibition of photochromic characteristics is desirable. Typically, the host material will be an organic material and preferably is a transparent or optically clear organic material. Such materials including, without limitation, a polymer, a copolymer, or mixtures thereof. Suitable host materials include, without limitation: poly(ally carbonate), polyepoxy, polyacrylates, polyethylene, polypropylene, polyvinyl chloride, polymethacrylates, poly ($C_1$–$C_{12}$)alkyl methacrylates, polyoxyalkylene methacrylates, cellulose acetate, cellulose triacetate, cellulose acetate butyrate, acetyl cellulose, poly (vinyl acetate), poly (vinyl alcohol), polyurethanes, polythiourethane, polysiloxane, polyamide, polystyrene, and copolymers including, without limitation, acrylates, methacrylates, methyl methacrylates, ethylene glycol bis methacrylate, vinyl acetate, vinyl butyral, urethane, thiourethane, diethylene glycol bis(ally carbonate), diethylene glycol dimethacrylate, diisopropenyl benzene, and the like and combinations thereof.

Typically, the compounds of the invention are incorporated into the host material by any convenient means, including, without limitation, dissolution, dispersion, polymerization with other components of the host material, incorporation into a coating applied to one surface of the organic host material, or combinations thereof. Alternatively, the compounds may be imbibed into the surface of the host material. Further more, the compounds may be coated onto the host material using various means such as spray coating, spin coating, spread coating, curtain coating, casing or dip coating.

The bis-naphthopyran compounds of the invention and mixtures thereof may be used in those applications in which organic photochromic substances are typically employed, such as optical lenses, and plano lenses, face shields, goggles, camera lenses, windows, automotive transparencies, inks, e.g., a liquid or paste containing photochromic dyes used for writing and printing, decorative objects such as plastic films and sheets, textiles, and coating compositions, e.g., paints, and verification marks on security documents, e.g., documents such as passports, driver's licenses, banknotes, and the like. Coating compositions are defined herein to include polymeric coating compositions prepared from materials such as polymethacrylate, polyurethane, polyepoxy resin and other resin used to produce synthetic polymers.

The amount of the bis-naphthopyran compound of the present invention used depends on the desired degree of darkening, provided that it is perceptible to the naked eye upon activation. Moreover, the particular amount used depends often upon the method used to incorporate or apply a photochromic substance. Typically, the more photochromic substance applied or incorporated, the greater is the color intensity up to a certain limit. In particular, it is used in a quantity of about 0.001 to about 20 weight percent based on the total weight of the object to be article.

The present invention is illustrated by the following examples, which are in no way intended to limit the scope of the present invention. Numerous modifications and variations will be apparent to those skilled in the art.

EXAMPLES

Example 1

Step 1

Tin (IV) chloride in methylene chloride (100 ml) was added dropwise under nitrogen with stirring to a ice-cooled solution of thiophene (6.5 g, 77 mmol) and p-methoxy benzoyl chloride (13.6 g, 79.8 mmol) in methylene chloride (50 ml). After addition, the reaction mixture was stirred further 10 minutes, then stirred at room temperature for 2.5 hrs, poured onto crushed ice (200 g). The organic layer was separated and the aqueous layer was extracted with methylene chloride (15 ml). The combined organic solutions were concentrated to remove most of the solvent. The residue was filtered through a plug of silica gel and washed with methylene chloride. Removal of solvent left a brown oil that was solidified on standing. Recrystallized from methylene chloride/hexane, colorless crystal was obtained. The mother liquid was de-colored with charcoal and recrystallized from methylenechloride/hexane and more crystal was obtained. A total of 16.48 g product was obtained (98%). Nuclear magnetic resonance ("NMR") spectra showed the resulted product has a structure consistent with p-methoxyphenyl-thiophene-2-yl-ketone.

Step 2

Sodium acetylide (1.37 g, 33.5 mmol) suspended in dry DMSO (25 ml) was added to p-methoxyphenyl-thiophene-2-yl-ketone (4.8 g, 22 mmol) in portions with stirring under water bath cooling while bubbling acetylene gas. After addition, the reaction mixture was stirred at room temperature for 2 hours, poured onto crushed ice, acidified with 4 M hydrochloric acid until the pH was approximately 6. After extraction with methylene chloride (20 ml, then 2×10 ml), the mixture was dried over anhydrous sodium sulfate and filtered. Evaporation of the solvent gave an oil that was purified by flush chromatography on neutral alumina (activity III) using hexane/methylene chloride (2:1) as eluent. De-coloration with a small amount of charcoal followed by removal of solvent afforded the relatively clean 1-(4-methoxyphenyl)-1-(thiophene-2-yl)prop-2-yn-1-ol as yellow-brown oil.

Step 3

1-(4-methoxyphenyl)-1-(thiophene-2-yl)prop-2-yn-1-ol from step 2 (257 mg, 1.05 mmol) was heated with 2-naphthol (144.2 mg, 1 mmol) in the presence of PPTS (0.05 mmol), and 3 Å molecular sieves in anhydrous 1,2-dichloroethane (5 ml) for two hours. Most of the solvent was removed in vacuo and the residue was filtered through a short silica gel column washed with methylene chloride. After removal of solvent and recrystallization from methylene chloride/hexane, a colorless solid was obtained (340 mg). NMR showed the resulted product has the structure consistent with 3-p-methoxyphenyl-3-(thiophene-2-yl)-[3H]-naphtho[2,1-b]pyran.

It was used as Comparative Example 1 described hereinafter.

Step 4

3-p-Methoxyphenyl-3-(thiophene-2-yl)-[3H]-naphtho[2,1-b]pyran from step 3 (175 mg, 0.5 mmol) in dry THF (4 ml) was cooled in dry ice-acetone bath under nitrogen. Butyl lithium (1.6 M, 0.5 ml) was added dropwise with stirring. The mixture was stirred for 0.5 hour, anhydrous cupric chloride (220 mg, 1.63 mmol) was added in one portion. Stirring was continued for 2 hours then slowly warm up to room temperature and stirred overnight. Crushed ice (10 g) was added to the reaction mixture. After acidification with 4M hydrochloric acid until the pH was approximately 1, the mixture was extracted with methylene chloride (25 ml, then 2×10 ml). The combined organic solution was dried over anhydrous sodium sulfate. If any solid was suspended in the methylene chloride, heating was used to dissolve the solid, cooled to room temperature and then dried. Subsequently, it was filtered and passed through a short silica gel column washed with methylene chloride. After removal of the methylene chloride until the total volume was approximately 5 ml, the mixture was heated to reflux, cooled down and allowed to stand at room temperature. The resulting solid was filtered and washed with a small volume of methylene chloride. The solid was collected and purified by chromatography on silica gel using hexane/methylene (1:1) and recrystallized from methylene chloride/hexane. 121 mg of a pink solid was obtained. NMR spectrum showed the product to have a structure consistent with 5,5'-bis[3-(p-methoxyphenyl)-[3H]-naphtho[2,1-b]pyran-3-yl]-2,2'-bithiophene.

Example 2

Step 1

The process of step 1 to step 3 in example 1 was followed except the substituent in the phenyl group is methyl instead of methoxy. NMR showed the resulted product has the structure consistent with 3-p-methylphenyl-3-(thiophene-2-yl)-[3H]-naphtho[2,1-b]pyran.

It was used as Comparative Example 2 described hereinafter.

Step 2

The process of step 4 in Example 1 was followed except 3-p-methylphenyl-3-(thiophene-2-yl)-[3H]-naphtho[2,1-b]pyran from step 3 (177 mg, 0.5 mmol) was used instead of 3-p-methoxyphenyl-3-(thiophene-2-yl)-[3H]-naphtho[2,1-b]pyran. Pink solid (136 mg) was obtained. NMR spectrum showed the product to have a structure consistent with 5,5'-bis[3-(p-methylphenyl)-[3H]-naphtho[2,1-b]pyran-3-yl]-2,2'-bithiophene.

Example 3

Step 1

The process of step 1 to step 3 of Example 1 was followed except that the substituent in the phenyl group is 4-fluoro instead of 4-methoxy. NMR showed the resultant product had a structure consistent with 3-p-fluorophenyl-3-(thiophene-2-yl)-[3H]-naphtho[2,1-b]pyran.

It was used as Comparative Example 3 described hereinafter.

Step 2

The process of step 4 of Example 1 was followed except 3-p-fluorophenyl-3-(thiophene-2-yl)-[3H]-naphtho[2,1-b]pyran from step 3 (180 mg, 0.5 mmol) was used instead of 3-p-methoxyphenyl-3-(thiophene-2-yl)-[3H]-naphtho[2,1-b]pyran. A yellow-brown solid (98 mg) was obtained. NMR spectrum showed the product to have a structure consistent with 5,5'-bis[3-(p-fluorophenyl)-[3H]-naphtho[2,1-b]pyran-3-yl]-2,2'-bithiophene.

Example 4

Step 1

The process of step 1 to step 3 of Example 1 was followed except the substituent in the phenyl group was 2-fluoro instead of 4-methoxy. NMR showed the resultant product has the structure consistent with 3-o-fluorophenyl-3-(thiophene-2-yl)-[3H]-naphtho[2,1-b]pyran.

It was used as Comparative Example 4 described hereinafter.

Step2

The process of step 4 of Example 1 was followed except 3-o-fluorophenyl-3-(thiophene-2-yl)-[3H]-naphtho[2,1-b]pyran from step 3 (180 mg, 0.5 mmol) was used instead of 3-p-methoxyphenyl-3-(thiophene-2-yl)-[3H]-naphtho[2,1-b]pyran. A pink solid (130 mg) was obtained. NMR spectrum showed the product to have a structure consistent with 5,5'-bis[3-(o-fluorophenyl)-[3H]-naphtho[2,1-b]pyran-3-yl]-2,2'-bithiophene.

Example 5

Step 1

Tin (IV) chloride in methylene chloride (100 ml) was added dropwise under nitrogen with stirring to a ice-cooled solution of bithiophene (2 g, 12 mmol) and p-methoxy benzoyl chloride (2.72 g, 16 mmol) in methylene chloride (25 ml). After addition, the reaction mixture was stirred further 10 minutes, and then stirred at room temperature for 2 hrs, poured onto crushed ice (100 g). The organic layer was separated. Aqueous layer was extracted with methylene chloride (15 ml). The combined organic solutions were concentrated to remove most of the solvent. The residue was filtered through a plug of silica gel and washed with methylene chloride/ethyl acetate (10:1). Removal of solvent left an oil which was solidified on standing. Recrystallized from methylene chloride/hexane generated yellow-green crystal (4.06 g). Nuclear magnetic resonance (NMR) spectrum showed the resulted product has the structure consistent with (2,2'-bithiophene-5-yl)-p-methoxyphenyl ketone.

Step 2

The process of step 2 in Example 1 was followed except (2,2'-bithiophene-5-yl)-p-methoxyphenyl ketone was used instead of p-methoxyphenyl-thiophene-2-yl-ketone. A yellow-brown oil was obtained. Nuclear magnetic resonance (NMR) spectrum showed the resulted product has the structure consistent with 1-(2,2'-bithiophene-5-yl)-1-(4-methoxyphenyl)prop-2-yn-1-ol.

Step 3

The process of step 3 in Example 1 was followed except that 1-(2,2'-bithiophene-5-yl)-1-(4-methoxyphenyl)prop-2-yn-1-ol was used instead of 1-(4-methoxyphenyl)-1-(thiophene-2-yl)prop-2-yn-1-ol. A light purple solid was obtained. NMR spectrum showed the product to have a structure consistent with 3-(2,2'-bithiophene-5-yl)-3-(p-methoxyphenyl)-[3H]-naphtho[2,1-b]pyran.

It was used as Comparative Example 5 described hereinafter.

Step 4

The process of step 4 in Example 1 was followed except that 3-(2,2'-bithiophene-5-yl)-3-(p-methoxyphenyl)-[3H]-naphtho[2,1-b]pyran (230 mg, 0.51 mmol) was used instead of 3-p-Methoxyphenyl-3-(thiophene-2-yl)-[3H]-naphtho[2,1-b]pyran. Yellow-green solid (191.6 mg) was obtained. NMR spectrum showed that the resulted product has the structure consistent with 5,5'''-Bis[3-(p-methoxyphenyl)-[3H]-naphtho[2,1-b]pyran-3-yl]-[2,2',5',2'',5'',2''']-quaterthiophene.

Example 6

Step 1

The process of step 1 in example 5 was followed except the 2-naphthoyl chloride (3.05 g, 16 mmol) was used instead of p-methoxy benzoyl chloride. A yellow solid (3.18 g) was obtained. NMR showed the resulted product has the structure consistent with (2,2'-bithiophene-5-yl)-(naphthalene-2-yl) ketone.

Step 2

The process of step 2 in Example 1 was followed except (2,2'-bithiophene-5-yl)-(naphthalene-2-yl) ketone was used instead of p-methoxyphenyl-(thiophene-2-yl)-ketone. A yellow-brown oil was obtained. NMR spectrum showed the resulted product has the structure consistent with 1-(2,2'-bithiophene-5-yl)-1-(naphthalene-2-yl)prop-2-yn-1-ol.

Step 3

The process of step 3 in Example 1 was followed except that 1-(2,2'-bithiophene-5-yl)-1-(naphthalene-2-yl)prop-2-yn-1-ol was used instead of 1-(4-methoxyphenyl)-1-(thiophene-2-yl)prop-2-yn-1-ol. A yellow orange solid was obtained. NMR spectrum showed the product to have a structure consistent with 3-(2,2'-bithiophene-5-yl)-3-(naphthalene-2-yl)-[3H]-naphtho[2,1-b]pyran.

It was used as Comparative Example 6 described hereinafter.

Step 4

The process of step 4 in Example 1 was followed except that 3-(2,2'-bithiophene-5-yl)-3-(naphthalene-2-yl)-[3H]-naphtho[2,1-b]pyran (237 mg, 0.5 mmol) was used instead of 3-p-Methoxyphenyl-3-(thiophene-2-yl)-[3H]-naphtho[2,1-b]pyran. A yellow-green solid (208 mg) was obtained. NMR spectrum showed that the resulted product has the structure consistent with 5,5'''-bis[(naphthalene-2-yl)-[3H]-naphtho[2,1-b]pyran-3-yl]-[2,2',5',2'',5'',2''']-quaterthiophene.

Analysis of Photochromic Properties.

The naphthopyran compounds of Examples 1 through 6 were dissolved in chloroform ($5.0 \times 10^{-5}$ mol/l), then exposed to UV irradiation at 366 nm for 4 minutes. UV spectra were recorded with Varian Cary 50 spectrometer. The molar extinction coefficient ($\epsilon$), absorption maxima ($\lambda$max) are given in Table 1.

Fatigue testing was conducted by exposing the solution of photochrome to UV irradiation (366 nm from 3 W UV lamp) and monitor the change of optical density at 1 hour interval. Prior to testing, the solution of photochrome was activated for 1 hour with UV irradiation. The saturated optical density ($\Delta$OD@ saturation) was taken by UV irradiation (366 nm) for 150 seconds.

TABLE 1

| Compound Example | $\lambda_{max}$/nm ($\epsilon$/dm$^{-3}$ mol$^{-1}$ cm$^{-1}$)* | $\lambda_{max}$/nm** |
|---|---|---|
| 1 | 306sh (25700), 318 (32340), 334sh (27610) | 534 |
| 2 | 306sh (25700), 318 (32340), 334sh (27610) | 530 |
| 3 | 306 (25480), 318 (32620), 332sh (27400) | 525 |
| 4 | 306sh (22490), 318 (30670), 336sh (25560) | 520, 580 |
| 5 | 304 (15280), 318 (17450), 366sh (28360), 407 (40300) | 560 |
| 6 | 305 (16660), 318 (17730), 366sh (28220), 410 (40780) | 555 |
| Comp. Ex. 1 | 304 (5830), 318 (6990), 347 (4750), 359 (4490) | 492 |
| Comp. Ex. 2 | 303 (5610), 318 (6930), 348 (4720), 359 (4420) | 480 |
| Comp. Ex. 3 | 304 (5590), 317 (6860), 347 (4580), 358 (4330) | 471 |
| Comp. Ex. 4 | 304 (5550), 317 (6720), 346 (4440), 357 (4260) | 459 |
| Comp. Ex. 5 | 307sh (20350), 318 (22830) | 525 |
| Comp. Ex. 6 | 307sh (21660), 318 (15510) | 522 |

*Absorption maxima of closed form.
**Absorption maxima of the opened form.

The results on table 1 show that compound I has a higher molar extinct coefficient and, thus, blocks more UV light than does compound VII.

TABLE 2

| Compound Example* | $\Delta$OD @ saturation | $T_{1/2}$ (hr)** |
|---|---|---|
| 3 | 0.70 | 14.6 |
| Comp. Ex. 3 | 0.58 | 6.5 |

*compound 3 ($5.0 \times 10^{-5}$ mol/l) and comparative example 3 ($1.0 \times 10^{-4}$ mol/l) in chloroform.
**Life time of photochrome under continuous irradiation with UV irradiation (366 nm) which is defined as the time till the change in optical density ($\Delta$OD) drops to the half of the initial value.

The results on Table 2 show that compound I provides more darkness and a much longer life than does compound VII.

What is claimed is:

1. A composition comprising a compound of the formula:

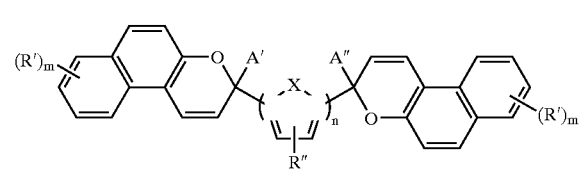

wherein X is sulfur or oxygen;

R', R" are the same or different and are each independently hydrogen, hydroxy, halogen, nitro, cyano, allyl, linear or branched ($C_1$–$C_{20}$)alkyl, ($C_3$–$C_{20}$)cycloalkyl, ($C_1$–$C_{20}$)alkoxy, ($C_1$–$C_{20}$)alkylacetylenyl, phenylacetylenyl, (C$_1$–C$_{20}$)alkenyl, phenylvinyl, halo (C$_1$–C$_{20}$)alkyl, halo(C$_3$–C$_{20}$)cycloalkyl, halo(C$_1$–C$_{20}$) alkoxy, aryl, aryloxy or heteroaryl optionally substituted with (C$_1$–C$_6$)alkyl or (C$_1$–C$_6$)alkoxy; arylalkyl or heteroarylalkyl; nitrogen-containing heterocyclic ring having 5 or 6 atoms optionally substituted (C$_1$–C$_6$) alkyl or (C$_1$–C$_6$)alkoxy, —N(R$_1$)R$_2$, CON(R$_1$)R$_2$, wherein R$_1$ and R$_2$ may be the same or different and are each independently hydrogen, (C$_1$–C$_{20}$)alkyl, (C$_3$–C$_{20}$) cycloalkyl, and optionally substituted phenyl; —OCOR, —COOR or —COR, wherein R represents hydrogen, (C$_1$–C$_{20}$)alkyl, (C$_3$–C$_{20}$)cycloalkyl, or aryl or heteroaryl optionally substituted with (C$_1$–C$_6$)alkyl or (C$_1$–C$_6$)alkoxy;

A', A" may be same or different and are each independently:
linear or branched (C$_1$–C$_{12}$)alkyl, (C$_3$–C$_{12}$)cycloalkyl, aryl(C$_1$–C$_6$)alkyl or heteroaryl(C$_1$–C$_6$)alkyl, (C$_1$–C$_6$)alkoxy(C$_1$–C$_6$)alkyl, (C$_1$–C$_{12}$)alkoxy, halo(C$_1$–C$_{12}$)alkyl, (C$_1$–C$_{12}$)haloalkoxy, (C$_1$–C$_{12}$) alkylthio;
optionally substituted aryl groups;
optionally substituted heteroaryl groups;
a group of the following formulae:

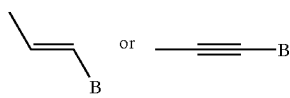

wherein B is hydrogen, (C$_1$–C$_{12}$)alkyl or optionally substituted aryl;
unsubstituted or mono-substituted pyrazolyl, pyridyl, imidazolyl, pyrazolinyl, imidazolinyl, or acridinyl, each of the said substituents selected from the group consisting of (C$_1$–C$_6$)alkyl, (C$_1$–C$_6$)alkoxy, fluoro, chloro, and phenyl.

(f) a group of the following formulae:

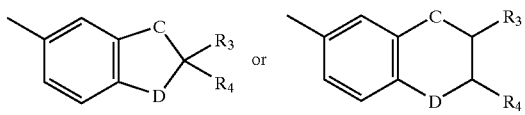

wherein C, D may be the same or different and are each independently carbon, oxygen, (C$_1$–C$_{12}$)alkyl nitrogen, or (C$_1$–C$_{12}$)acyl nitrogen;
R$_3$ and R$_4$ are each hydrogen or (C$_1$–C$_{12}$)alkyl; and wherein the phenyl moiety is optionally substituted with (C$_1$–C$_{12}$)alkyl, (C$_1$–C$_{12}$)alkoxy, (C$_2$–C$_{12}$)acyl, fluoro, or chloro;
n is an integer from 1 to 8; and
m is an integer from 0 to 3; and
a photochromic compound selected from the group consisting of naphthopyran, spirooxazine, one or more nonphotochromic dyes, or a combination thereof.

2. The composition of claim 1, wherein:
X is sulfur or oxygen;
R', R"are the same or different and are each independently hydrogen, nitro, cyano, allyl, fluoro, chloro, bromo, trifluoromethyl, trichloromethyl, pyrrolidino, piperidino, morpholino, phenyl, benzyl; linear or branched (C$_1$–C$_6$)alkyl, (C$_1$–C$_6$)alkoxy, or —OCOR or —COOR wherein R is hydrogen, (C$_1$–C$_6$)alkyl, (C$_3$–C$_6$)cycloalkyl;

A', A"are the same or different and are each independently:
linear or branched (C$_1$–C$_6$)alkyl, (C$_3$–C$_6$)cycloalkyl, aryl(C$_1$–C$_4$)alkyl or heteroaryl(C$_1$–C$_4$)alkyl, (C$_1$–C$_6$)alkoxy(C$_1$–C$_6$)alkyl;
unsubstituted, mono-, di-substituted aryl selected from phenyl or naphthyl;
unsubstituted or mono-substituted heteroaryl groups that are furyl, thienyl, pyrryl, indolyl, benzofuryl, benzothienyl, pyridyl, dibenzofuryl, dibenzothienyl, or carbazolyl the substituents being nitro, amino, cyano, hydroxy, epoxy, hydroxyethoxy, methoxyethoxy, hydroxyethoxyethoxy, methoxyethoxyethoxy, fluoro, chloro, bromo, iodo, vinyl, allyl, trifluoromethyl, phenyl, (C$_1$–C$_6$)alkyl, (C$_1$–C$_6$)alkoxy, cyclo(C$_3$–C$_6$)alkyl, cyclo(C$_1$–C$_6$) alkoxy, (C$_1$–C$_6$)alkylamino, di(C$_1$–C$_6$)alkylamino, diarylamino, phenylacetylenyl, or phenylvinyl;
N(C$_1$–C$_6$)alkylpiperazino, N-aryl-piperizino, aziridino, indolino, pyrrolidino, pyrrolino, piperidino, (C$_1$–C$_4$) alkylpiperidino, di(C$_1$–C$_4$)alkylpiperidino, 4-piperidinopiperidino, morpholino, 2,6-di(C$_1$–C$_4$) alkylmorpholino, thiomorpholino, thioazolidino, tetrahydroquinolino, or pyrryl;
N(R$_1$)R$_2$, CON(R$_1$)R$_2$, wherein R$_1$and R$_2$ are the same or different and are each independently hydrogen, (C$_1$–C$_6$)alkyl, (C$_3$–C$_6$)cycloalkyl, phenyl or —COR, —OCOR or —COOR wherein R is hydrogen, (C$_1$–C$_6$)alkyl, (C$_3$–C$_6$)cycloalkyl, or phenyl;
n is an integer from 1 to 6; and
m is an integer from 0 to 2.

3. The composition of claim 1, wherein:
X is sulfur;
R', R"are the same or different and are each independently hydrogen, nitro, cyano, fluoro, chloro, bromo, pyrrolidino, piperidino, morpholino, phenyl, benzyl, (C$_1$–C$_4$)alkyl, or (C$_1$–C$_4$)alkoxy;
A', A"are the same or different and are each independently:
a linear or branched (C$_1$–C$_4$)alkyl, (C$_3$–C$_6$)cycloalkyl; unsubstituted, mono-, or di-substituted phenyl the substituents being one or more of nitro, amino, acyl, cyano, methoxy, ethoxy, methoxyethoxy, fluoro, chloro, vinyl, allyl, methoxycarbonyl, ethoxycarbonyl, (C$_1$–C$_4$)alkyl, di(C$_1$–C$_4$) alkylamino, piperazino, piperidino, arylperidino, morpholino, pyrrolidino, aziridino, acryloxy, methacryloxy, phenylacetylenyl, phenylvinyl;
unsubstituted or mono-substituted furyl, thienyl, or pyrryl substituted with a substituent that is (C$_1$–C$_4$) alkyl or phenyl;
n is an integer from 1 to 4, and
m is, independently, integer from 0 to 2.

4. A composition comprising a compound selected from the group consisting of:
5,5'-Bis[3-(p-methoxyphenyl)-[3H]-naphtho[2,1-b] pyran-3-yl]-2,2'-bithiophene;
5,5'-Bis[3-(p-methylphenyl)-[3H]-naphtho[2,1-b]pyran-3-yl]-2,2'-bithiophene;
5,5'-Bis[3-(p-fluorophenyl)-[3H]-naphtho[2,1-b]pyran-3-yl]-2,2'-bithiophene;
5,5'-Bis[3-(o-fluorophenyl)-[3H]-naphtho[2,1-b]pyran-3-yl]-2,2'-bithiophene;
5,5'''-Bis[3-(p-methoxyphenyl)-[3H]-naphtho[2,1-b] pyran-3-yl]-[2,2',5',2'',5'',2''']-quaterthiophene;

5,5'''-Bis[3-(naphthalene-2-yl)-[3H]-naphtho[2,1-b]pyran-3-yl]-[2,2',5',2'',5'',2''']-quaterthiophene; or 5,5'''-Bis[3-(o-fluorophenyl)-[3H]-naphtho[2,1-b]pyran-3-yl]-[2,2',5',2'',5'',2''']-quaterthiophene and a photochromic compound selected from the group consisting of naphthopyran, spirooxazine, one or more non-photochromic dyes, or a combination thereof.

* * * * *